(12) United States Patent
Clark

(10) Patent No.: US 6,748,801 B2
(45) Date of Patent: Jun. 15, 2004

(54) SUBSTRATE BENDING STIFFNESS MEASUREMENT METHOD AND SYSTEM

(75) Inventor: Robert A. Clark, Webster, NY (US)

(73) Assignee: Xerox Corporation, Stamford, CT (US)

(*) Notice: Subject to any disclaimer, the term of this patent is extended or adjusted under 35 U.S.C. 154(b) by 48 days.

(21) Appl. No.: 10/440,752

(22) Filed: May 19, 2003

(65) Prior Publication Data

US 2003/0205093 A1 Nov. 6, 2003

Related U.S. Application Data

(62) Division of application No. 10/041,047, filed on Jan. 7, 2002, now Pat. No. 6,581,456.

(51) Int. Cl.[7] .................................................. G01L 5/04
(52) U.S. Cl. .......................... 73/159; 271/259; 271/261; 271/98; 399/90; 399/130
(58) Field of Search .......................... 73/159, 160, 849, 73/852; 271/258.01, 259–262, 98–106; 399/130, 90

(56) References Cited

U.S. PATENT DOCUMENTS

| | | |
|---|---|---|
| 4,866,984 A | 9/1989 | Houghton |
| 4,991,432 A | 2/1991 | Houghton et al. |
| 5,138,178 A | 8/1992 | Wong et al. |
| 5,297,062 A | 3/1994 | Cresson et al. |
| 5,461,468 A * | 10/1995 | Dempsey et al. ............ 399/396 |
| 5,867,393 A * | 2/1999 | Richardson et al. ......... 700/223 |
| 5,921,540 A | 7/1999 | Acquaviva et al. |
| 5,967,511 A * | 10/1999 | Bell ............................ 271/252 |
| 6,264,188 B1 | 7/2001 | Taylor et al. |
| 6,352,255 B1 | 3/2002 | Taylor |
| 6,398,206 B1 | 6/2002 | Yang et al. |
| 6,398,207 B1 | 6/2002 | Taylor et al. |
| 6,398,208 B1 | 6/2002 | Yang et al. |

* cited by examiner

Primary Examiner—Edward Lefkowitz
Assistant Examiner—Alandra Ellington

(57) ABSTRACT

A sheet separation and feeding system for measuring substrate bending stiffness and thereby basis weight on a real time basis. Provided is a corrugator having a plurality of parallel ribs, with one or more sheets of the substrate provided below the corrugator wherein a predetermined gap exists between a topmost sheet of the sheets and the corrugator. A vacuum is applied between the corrugator and the topmost sheet, wherein the vacuum is sufficiently large to raise the topmost sheet, thereby deflecting and bending it into a profile corresponding to the arrangement and size of the corrugator ribs and bending stiffness of the substrate. One or more sensors are provided for measuring the deflection of the topmost sheet. The vacuum, an air knife output and/or a fluffer output are then adjusted according to predetermined rules and the measured deflection.

10 Claims, 5 Drawing Sheets

SUBSTRATE BENDING STIFFNESS MEASUREMENT METHOD AND SYSTEM

This is a divisional of U.S. application Ser. No. 10/041,047 filed Jan. 7, 2002 now U.S. Pat. No. 6,581,456 by the same inventors, and claims priority therefrom. This divisional application is being filed in response to a three-way restriction requirement in that parent application and contains rewritten and additional claims to the restricted-out subject matter of original claims 9–14.

Especially with the advent of high speed xerography reproduction machines wherein copiers or printers can produce at a rate in excess of one hundred and twenty pages per minute (PPM), there is a need for sheet handling systems to feed paper or other substrate through each process station in a rapid succession in a reliable and dependable manner in order to utilize the full capabilities of the reproduction machine. These sheet handling systems must operate flawlessly to virtually eliminate the risk of damaging the substrate and to minimize machine shutdowns due to misfeeds or multifeeds. It is in the initial separation of the individual sheets from the substrate stack where the greatest number of problems occur.

One of the sheet feeders best known for high speed operation is the top vacuum corrugation feeder with front air knife. In this system, a vacuum plenum with a plurality of friction belts arranged to run over the vacuum plenum is placed at the top of a stack of sheets in a supply tray. Several fluffers are located around the perimeter of the stack for injecting air into the top of the stack. When vacuum is supplied to the vacuum plenum, the resulting vacuum field draws one or more sheets against the friction belts. At the front of the stack, an air knife is used to inject air into the acquired sheets to separate the top sheet from the remainder of the sheets which then are pushed down onto the stack. In operation, the vacuum pulls one or more sheets up and acquires them, and then air is injected by the air knife toward the acquired sheets to separate the top sheet. Following separation, the-belt transport drives the sheet forward off the stack of sheets. In this configuration, separation of the next sheet cannot take place until the top sheet has cleared the stack. In this type of feeding system every operation takes place in succession or serially and therefore the feeding of subsequent sheets cannot be started until the feeding of the previous sheet has been completed.

A variation of the paper feeder technology described above uses a reciprocating feedhead in lieu of a friction belt transport to drive the top sheet into the paper path, e.g., U.S. Pat. No. 6,264,188. At the appropriate time during the feed cycle, the feedhead moves towards take away rolls, carrying the acquired top sheet with it. The leading edge of the top sheet then enters the take away roll nip, and the take away rolls remove the sheet from the feedhead, which then cycles back to its original position. Within the feedhead are several parallel ribs which induce a corrugation pattern in the acquired sheets, thus creating gaps between the sheets, facilitating sheet separation by the air knife.

Current top and bottom vacuum corrugation feeders may utilize a valved vacuum feedhead, e.g., U.S. Pat. No. 4,269,406. At the appropriate time during the feed cycle the valve is actuated, establishing a flow and hence a negative pressure field over the stack top or bottom if a bottom vacuum corrugation feeder is employed. This field causes the movement of the top sheet(s) to the vacuum feedhead where the sheet is then transported to the take away rolls. Once the sheet feed edge is under control of the take away rolls, the vacuum is shut off. The trail edge of this sheet exiting the feedhead area is the criteria for again activating the vacuum valve for the next feeding.

Sheet feeding with apparatus for measuring substrate bending stiffness and thereby basis weight on a real time basis is provided in the disclosed embodiment. A corrugator having a plurality of parallel ribs is provided, with one or more sheets of the substrate provided below the corrugator wherein a predetermined gap exists between a topmost sheet of the sheets and the corrugator. A vacuum is applied between the corrugator and the topmost sheet wherein the vacuum is sufficiently large to raise the topmost sheet thereby deflecting and bending it into a profile corresponding to the arrangement and size of the corrugator ribs and bending stiffness of the substrate. One or more sensors are provided for measuring the deflection of the topmost sheet. The vacuum, an air knife output and/or a fluffer output are then adjusted according to predetermined rules and the measured deflection.

Figure 1:
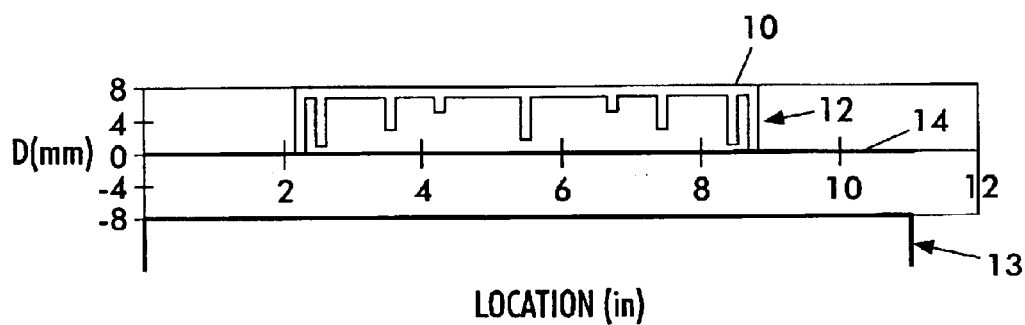
FIG. 1 is one example of a feedhead corrugator and two sheets of substrate prior to application of a vacuum.

For a general understanding of the features of the present invention, reference is made to the drawings. In the drawings, like reference numerals have been used throughout to designate like elements. It will become evident from the following discussion that the present invention and the various embodiments set forth herein are suited for use in a wide variety of printing and copying systems, and are not necessarily limited in application to the particular systems shown herein.

Printing and copying systems utilizing a vacuum to acquire a sheet of paper or other substrate from a stack have employed a corrugated contact surface feedhead composed of a combination of variant sized ribs to reduce the bonding forces between paper surfaces, thereby separating sheets on the contact surface to reduce the likelihood of removing other sheets from the stack (i.e., to reduce multi-feeds).

Figure 2:
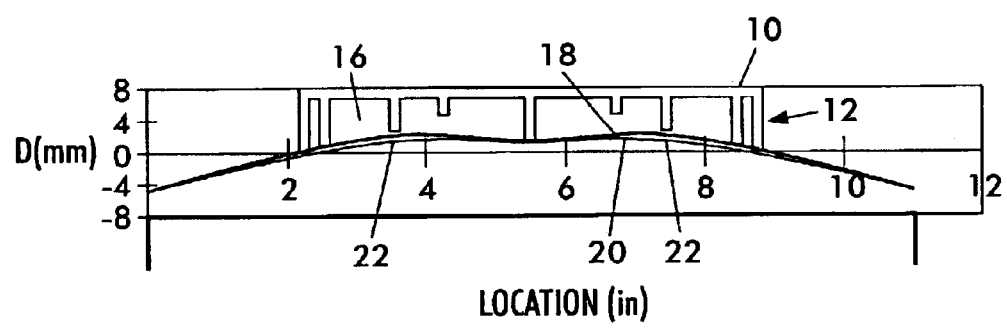
FIG. 2 is a feedhead corrugator and two sheets of 300 gsm paper subsequent to application of a vacuum.

It is well known in the art that there are bonding forces between substrate surfaces, either due to vacuum, electrostatic, or edge wedding forces or other sources. In a vacuum feeder, to separate one sheet of substrate from another, air is blown into the space between multiply acquired sheet surfaces, so that there are essentially two steps in sheet separation in a vacuum feeder: one is to generate a gap and the other is to blow air into the gap. The latter function is performed by air knives. Without a corrugator, applying only a uniform vacuum to pull sheets apart is very unreliable and if more than one sheet is acquired to a flat vacuum substrate contact surface, a serious problem occurs because there is no meaningful force to separate the sheets acquired except gravity, which will not guarantee a sheet separation. To break up the paper bond to initiate gaps, it is beneficial to have an additional stress acting on the substrate surfaces, and the ribs of the corrugated contact surface are instrumental in providing additional stress to separate sheets of substrate. FIGS. 1 and 2 show sheet separation of a 300 gsm heavyweight paper during a prefeed acquisition phase. A corrugator 10 having ribs 12 is positioned above a stack 13 of the heavyweight paper where, for clarity, only the two topmost acquired sheets 14 are shown at the instant before sheet deflection occurs. In FIG. 2, a vacuum applied to the open space 16 between the corrugator 10 and the acquired sheets 14 causes the first sheet 18 and the second sheet 20 to be drawn toward the corrugator while creating a gap 22 between the first and second sheets. The vacuum which was used to acquire the first sheet 18 forces the sheet to conform to the ribs. Since any additional acquired sheets are not subjected to the full vacuum from the feedhead, the additional sheets do not deform nearly as much as they are pulled against the ribs. The gap 22 provides a space for an air knife (not shown) to blow air in order to further separate the first and second sheets, 18 and 20, causing the second sheet to fall back onto the stack 13 before forward feeding the first sheet to the next station in the system.

Figure 3:
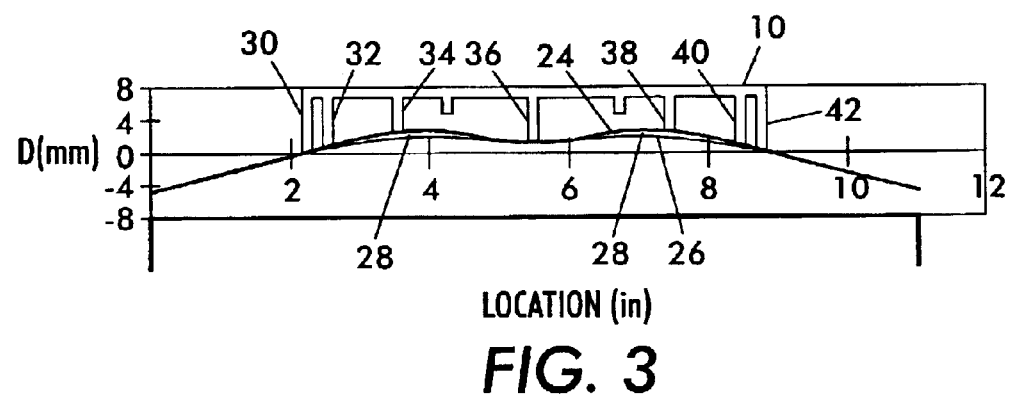
FIG. 3 is a feedhead corrugator and two sheets of 110# paper subsequent to application of a vacuum.

A major challenge in developing any substrate handling subsystem is to accommodate a wide variety of substrates without any information from the user. FIGS. 3–6 illustrate the effects of applying a constant vacuum between the corrugator 10 and the two topmost acquired sheets 14 during a prefeed acquisition phase for a variety of substrates having different basis weights and bending stiffnesses. FIG. 3 shows the bending profile for heavyweight paper of a first 110# sheet 24 and a second 110# sheet 26 and the resulting 110# gap 28. The first 110# sheet 24 is observed to be in contact with seven corrugator ribs 30, 32, 34, 36, 38, 40 and 42. The 110# gap 28 is also observed to be sufficiently large for an air knife to induce further separation of first and second sheets 24 and 26.

Figure 4:
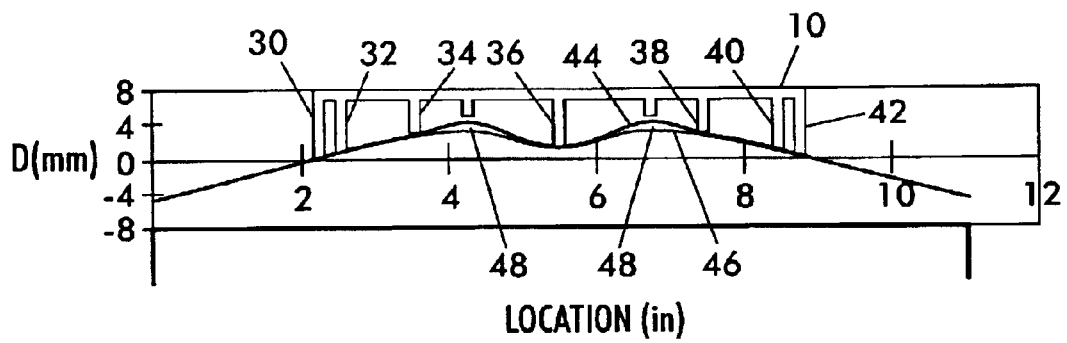
FIG. 4 is a feedhead corrugator and two sheets of 32# paper subsequent to application of a vacuum.

FIG. 4 illustrates the bending profile for 32# paper of a first sheet 40 and a second sheet 42 and the resulting 32# gap 44. The first 32# sheet 40 is observed to be in contact with the same seven corrugator ribs 30, 32, 34, 36, 38, 40 and 42 contacted by the first 110# sheet 24. The 32# gap 48 is again observed to be sufficiently large for an air knife to induce further separation of first and second sheets 44 and 46 without excessive bending of the first and second sheets 44 and 46.

Figure 5:
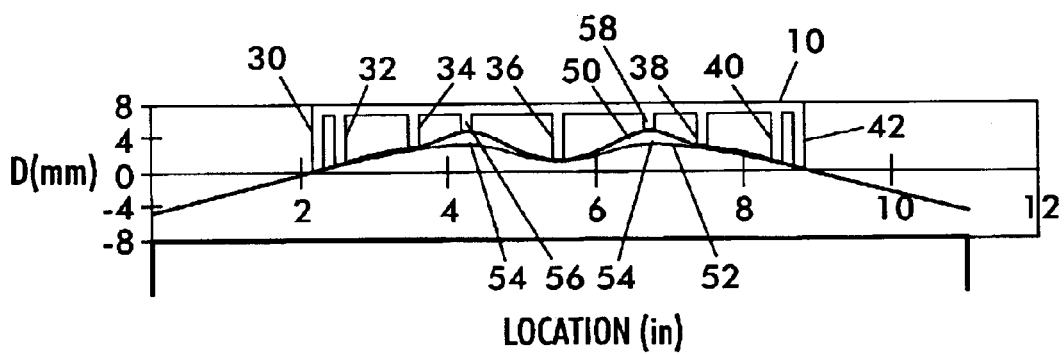
FIG. 5 is a feedhead corrugator and two sheets of 20# paper subsequent to application of a vacuum.

FIG. 5 depicts the bending profile for a medium weight 20# paper of a first sheet 50 and a second sheet 52 and the resulting 20# gap 54. The first 20# sheet 50 is observed to be in contact with all nine corrugator ribs including the seven corrugator ribs 30, 32, 34, 36, 38, 40 and 42 and, additionally, ribs 56 and 58.

Figure 6:
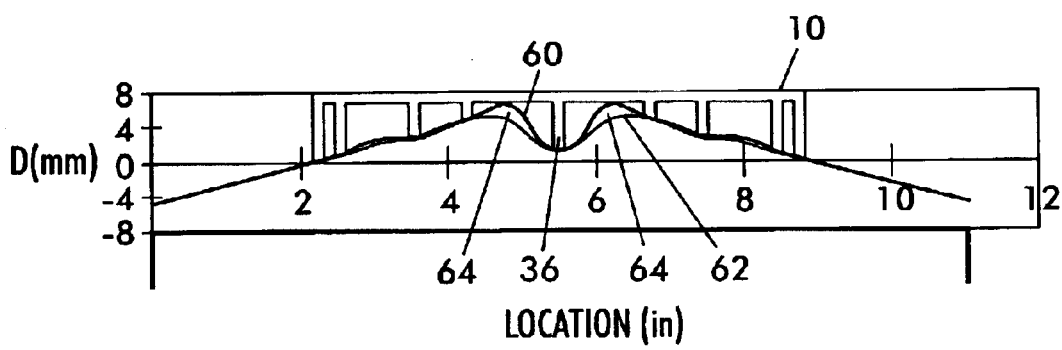
FIG. 6 is a feedhead corrugator and two sheets of 13# paper subsequent to application of a vacuum.

FIG. 6 shows the bending profile for a lightweight 13# paper of a first sheet 60 and a second sheet 62 and the resulting 13# gap 64. The top sheet 60 now exhibits much more bending than occurred with the heavier weight sheets, however, the points of maximum separation between the first two sheets 60 and 62, as observed in gap 64, advantageously remains near the center rib 36 which provides a consistent target area for an air knife which will maintain good efficacy in regards to dropping of the second sheet 62 back onto the stack 13.

It is evident from FIGS. 3–6 that the correct vacuum level, fluffer output, and air knife output are a function of the basis weight of the paper or other substrate being acquired by corrugator 10. It should be noted, however that while adjusting the vacuum according to the bending stiffness is possible, it is sufficient to only adjust the fluffer and perhaps the air knife outputs. If the vacuum is variable, a lookup table would also need to compensate for the fact that the deflection of the top sheet is directly proportional to the applied vacuum, otherwise a misidentification of the paper might occur in any measurements based on bending which take place after the vacuum is changed. In fact, in simpler embodiments, it is not necessary to provide an infinitely adjustable, or continuously variable, air knife or fluffer output levels. This fact is evidenced by FIG. 7 which provides a distribution of sensor output voltages for a number of different runs indicating the height of a topmost sheet of paper after being acquired by corrugator 10. To obtain this data, an analog sensor was installed in corrugator 10 to produce an output voltage corresponding to the peak height of the first sheet of paper after being acquired to the corrugator by a constant vacuum.

Figure 7:
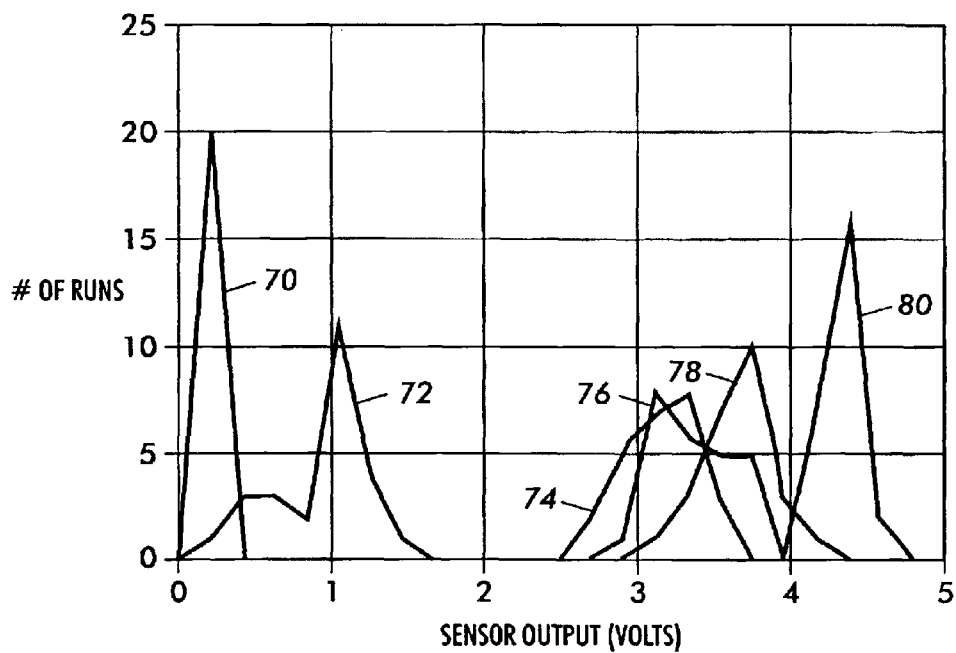
FIG. 7 is a distribution of sensor output voltages for various paper basis weights for a number of runs.

A number of runs were performed with each of selected weights of paper and a probability distribution was calculated for each selected weight with the results graphed in FIG. 7. Graph segment 70 represents sensor output distribution for a 51 gsm paper, segment 72 represents sensor output for a 75 gsm paper, segment 74 represents sensor output for a 90 gsm paper, segment 76 represents sensor output for a 105 gsm paper, segment 78 represents sensor output for a 120 gsm color paper, and segment 80 represents sensor output for a 120 gsm text paper.

It is readily apparent from FIG. 7 that there are two major groupings of paper weights. Segments 70 and 72 representing paper weights of 75 gsm or less and segments 74–80 representing paper weights of 90 gsm or more. In the interest of efficiency and economy, therefore, it is possible to design, for one embodiment, a vacuum corrugated feeder optimized for two groups of paper weight ranges. Such a system can have a single switch point for selecting between one of two settings of vacuum level, fluffer output and/or air knife output. The present concept facilitates this task by enabling on-line measurement of the substrate bending stiffness while the sheet is corrugated by a VCF (vacuum controlled feeder) feedhead. Using this information, the paper feeder and other paper handling subsystems can be optimized for the substrate currently being used in real time.

Figure 8:
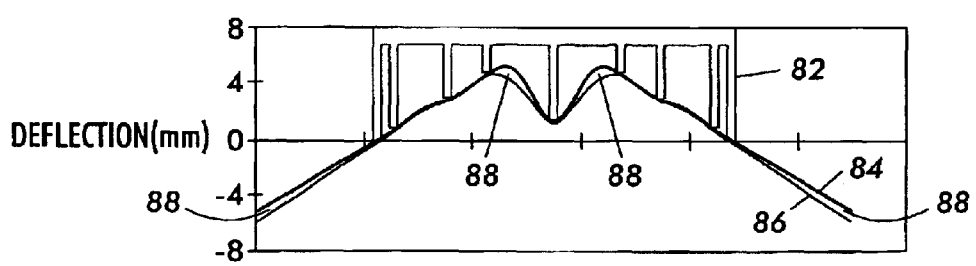
FIG. 8 is an alternate feedhead corrugator and two sheets of 75 gsm (20# bond) paper subsequent to application of a vacuum.

For the simplest case where the system is designed for two groups of paper weights, or bending stiffnesses, a simple optical sensor may be employed which selects a lower vacuum level, fluffer output and/or air knife output whenever an optical line of sight is broken by the first sheet of paper being raised above a predetermined point. Alternately, a more complicated sensor arrangement utilizing analog or digital sensors may be employed providing a system of continuously variable settings, or discrete settings in finer increments. FIG. 8 shows a corrugator 82 design that is particularly effective for use with an embodiment of the present invention wherein the height of the first sheet 84 can be readily detected by a sensor. Two 75 gsm sheets, 84 and 86, are acquired to a feedhead corrugator 82 using multiple ribs. As the second sheet is not subjected to the same magnitude of vacuum as the top sheet, the second sheet deflects less and begins to slip off the top sheet. During this process, intersheet gaps 88 are created at the lead edge and near the center, which allows air to flow in between the two sheets. The sheets then separate, with the second sheet falling back onto the stack.

The degree of deflection is also dependent on the bending stiffness of the paper. Given the same level of vacuum, a lightweight paper such as 16# bond will deform, or corrugate, much more than a heavy paper such as 100# uncoated cover stock. Embodiments of the present invention describe a method where the amount of corrugation is measured to obtain an estimate of the basis weight of the paper.

Figure 9:
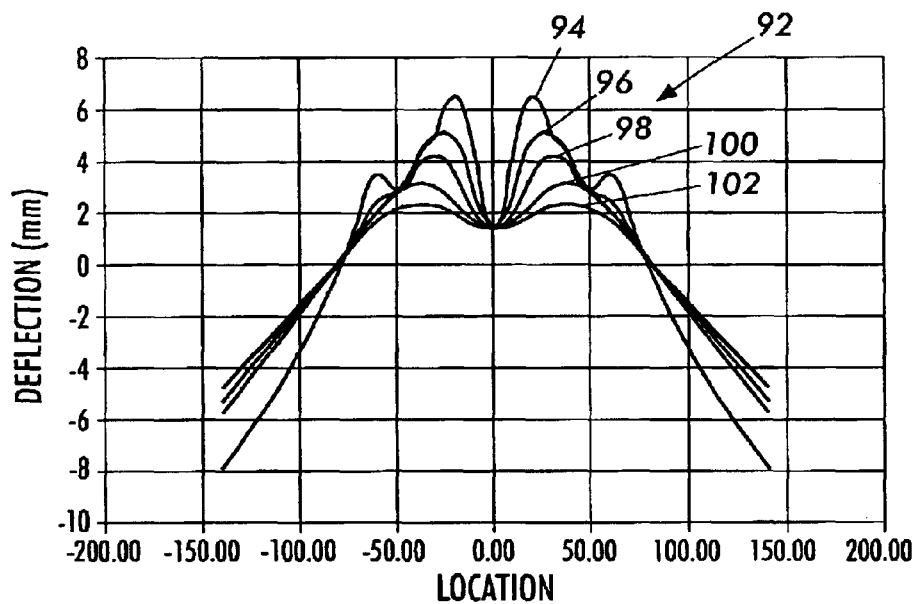
FIG. 9 is a graph of bending profiles for papers of a variety of basis weights.

FIG. 9 gives the top sheet deflection profiles 92 generated by a Multiple Vacuum Corrugation Feeder (MVCF) for various basis weights. Profile 94 represents 50 gsm (13# bond) paper, profile 96 represents 75 gsm (20# bond) paper, profile 98 represents 120 gsm (80# offset) paper, profile 100 represents 203 gsm (110# index) paper, and profile 102 represents 300 gsm (110# cover) paper. The MVCF uses several ribs to create multiple corrugations in the top sheet to enable better separation. A 2-D finite element model (a method well known in the art) is generated to determine the optimum location and size of the ribs, and the curves given in FIG. 9 are partial results from the analysis.

Figure 10:
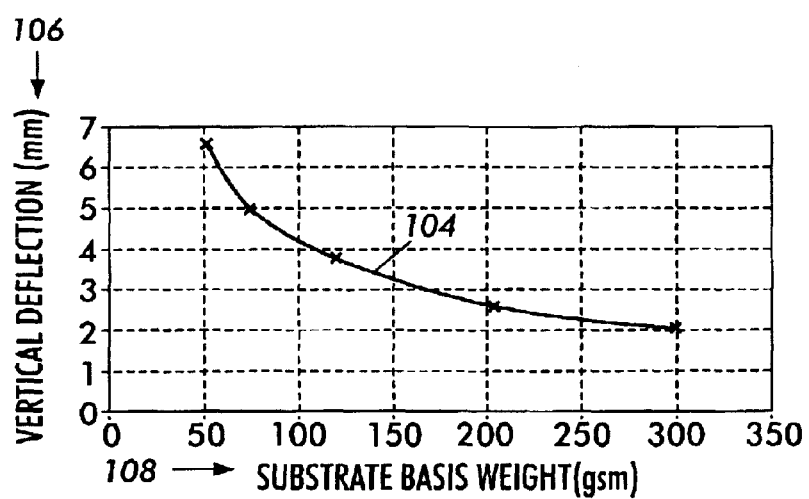
FIG. 10 is a graph of substrate deflection versus substrate basis weight.

Upon inspection of FIG. 9, it can be readily seen that there is an inversely proportional relationship between the basis weight and the maximum deflection of the top sheet. By placing a displacement sensor about 20 mm from the feedhead centerline, it is possible to use the measured vertical displacement (no corrugation to full corrugation) to determine the stiffness of the paper. FIG. 10 indicates how this displacement relates to the basis weight. Curve 104 represents the vertical deflection profile 106 versus the substrate basis weight 108. Using a lookup table, a microcontroller looks up preferred operating parameters and adjusts the vacuum level, fluffer pressure, and/or air knife pressures to optimal values for the paper being fed. As described above, if only two different air knife/fluffer pressure settings are required, the displacement sensor may only need to be comprised of a simple on/off optical sensor and a mechanism which "breaks the beam" of the sensor if the sheet deflects more than a set amount.

It is to be noted that the system optionally defaults to a worst-case scenario, heavyweight substrate, before acquiring the initial sheet at the start of a run. The system then may tune itself dynamically in real time according to measurements of the initial and subsequent sheets of substrate. The system may perform adjustments during acquisition of the initial sheet where system response time is sufficiently small, or it may perform adjustments following acquisition of the initial sheet. This concept facilitates providing a system wherein no user input is required to determine the weight or bending stiffness of the substrate.

There have been previous inventions developed to accomplish this task. In U.S. Pat. No. 5,138,178, Lam F. Wong et al describe a photoelectric paper basis weight sensor which presumes that the amount of energy transmitted through the substrate is inversely proportional to the basis weight. While this is true for uncoated papers, the higher reflectivity of coated papers and low opacity of transparencies "fool" such a system into estimating a higher or lower basis weight than what is actually true. Also, when the bending stiffness of uncoated and coated papers are compared, coated papers are less stiff compared to uncoated papers of the same basis weight. As the embodiments described herein measure the deflection of the paper, the bending stiffness is directly obtained via elastic theory. Furthermore, the bending stiffness is a more useful quantity for optimizing paper handling subsystems than the basis weight. For example, it is important for the leading edge of a sheet of paper to be correctly aligned when entering a process station which is primarily a function of bending stiffness whenever the path is other than a straight line path.

Other methods for bending stiffness measurement include bending the paper a set distance and measuring the force (U.S. Pat. Nos. 4,866,984 & 4,991,432) and using pressure differences to deform the sheet and then measuring the corresponding deflections (U.S. Pat. No. 5,297,062). These methods, however, require more complex hardware to perform the same task and are not suited to measuring the bending stiffness of substrate being drawn off the top of a stack at a high frequency rate. Embodiments of the present invention may make use of an existing feedhead to produce the deflection required to calculate the bending stiffness of the substrate. In the case described above, only an optical sensor and a simple linkage are required.

Implementing the paper stiffness sensor enables the use of lower pressure settings for low to medium weight papers that are most often used in an office setting. It also, thereby, reduces the electrical power consumed by the air blowers, resulting in a lower operating cost for the customer. These lower pressure settings further result in the blowers producing less noise, which is also another important customer consideration. Concepts of the present invention also act to eliminate the potential need for the customer to indicate what type of paper is currently being used, thereby eliminating a source of error. It is also noted, as the bending stiffness more directly relates to paper handling performance, a product whose subsystems are optimized using these techniques are more robust resulting in fewer paper-related failures. Flutter problems associated with using too high air pressures for a given paper weight or bending stiffness are also reduced.

A system using concepts described herein may be tuned to operate at a better energy efficiency by reducing the energy consumed for lightweight papers. For example, the basis weight information available from the sensor or lookup table can be used for the finishing device of a reprographic system. In a xerographic system, a fuser needs to generate a certain amount of heat that is used to fuse the toner onto the substrate (the paper). The thicker the sheet is, the more heat that must be generated because, in order to achieve the fuse temperature, the thermal capacity of the substrate must be overcome. It takes a heavyweight paper longer to heat than a lightweight paper, thus requiring a greater quantity of heat. Without knowing the basis weight of the substrate, a worst-case setting must be used, thereby wasting energy. The present invention lends itself to providing a self-tuning system whereby the amount of fuser heat generated is adjusted real time according to the basis weight of the substrate where the basis weight is estimated according to the measured bending stiffness of the substrate. Other substrate handling subsystems dependent on the bending stiffness or basis weight of the substrate may also be self-tuned without any user input.

Figure 11:
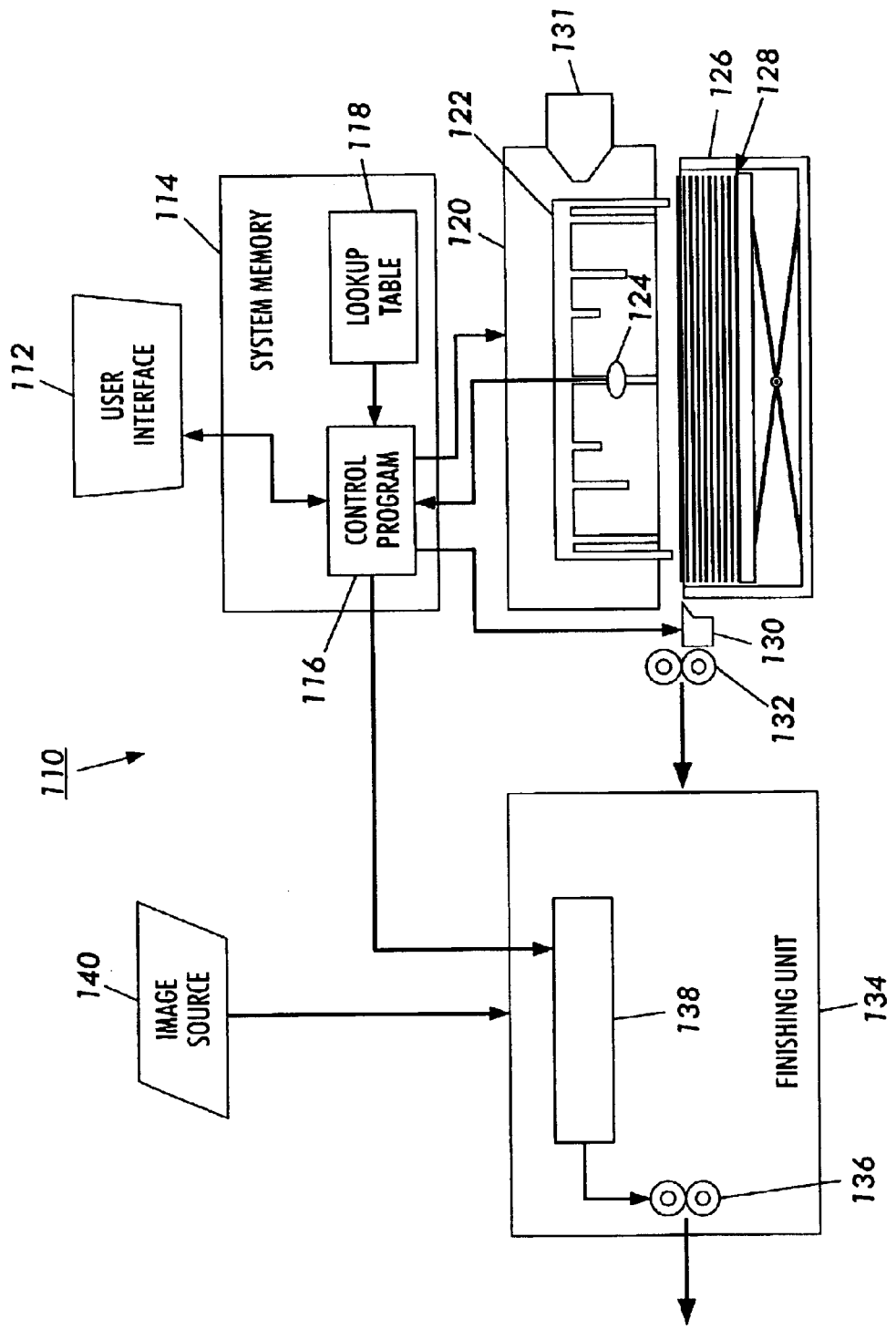
FIG. 11 is a representational schematic of an exemplary reprographic system according to the present invention.

With attention toward FIG. 11, a reprographic system 110 is shown in schematic form that is suitable for embodiments of the present invention. The system includes a user interface 112, system memory 114 into which are incorporated a control program 116 and a lookup table 118, a vacuum source 120, a feedhead corrugator 122, a sensor arrangement 124, a substrate/paper tray 126 for a stack of substrate 128, an air knife 130, a fluffer 131, a forward feeding unit 132, a finishing unit 134, a fuser 136, a fuser temperature control 138, and an image source 140. The system is shown in a representational schematic form as the components illustrated are well known in the art. The image source may be a scanning device or a network connection for receiving images from a digital network. The sensor arrangement 124 may be digital or analog and may provide a continuous output representing first sheet height, or may provide discrete output representing one or more heights for the first sheet. Sensor arrangement 124 may be designed as a single sensor or as multiple sensors. The control program is configured to utilize sensor arrangement 124 and the lookup table 118 as previously described.

While the invention has been described with respect to specific embodiments by way of illustration, it is to be understood that the appended claims cover all such modifications and changes which fall within the true spirit and scope of the invention.

What is claimed is:

1. A pneumatic sheet separation and feeding system including a sheet feedhead for separating and feeding the top sheet from a stack of print substrate sheets of variable sheet beam strengths and a pneumatic system for attracting the top sheet against said sheet feedhead, wherein said sheet feedhead has a plurality of differentially spaced extending ribs of different rib extensions which provide differently shaped pneumatic deformations of the top sheet against said sheet feedhead ribs depending on said sheet beam strength of the top sheet.

2. The pneumatic sheet separation and feeding system of claim 1, wherein said differentially spaced ribs of different ribs of said sheet feedhead are substantially parallel to one another.

3. The pneumatic sheet separation and feeding system of claim 1, wherein said sheet feedhead further includes a sheet deformation sensor system for detecting said differently shaped pneumatic deformations of the top sheet against said sheet feedhead ribs depending on said sheet beam strength of the top sheet to provide an estimation of the sheet beam strength of the top sheet.

4. The pneumatic sheet separation and feeding system of claim 3, wherein said control program utilizes said estimation of the sheet beam strength of the top sheet via a lookup table to control at least one preferred pneumatic operating parameter of said pneumatic sheet separation and feeding system.

5. The pneumatic sheet separation and feeding system of claim 3, wherein said control program utilizes said estimation of the sheet beam strength of the top sheet via a lookup table to control a sheet fuser.

6. A vacuum corrugating sheet feeder system comprising:
   a sheet corrugator feedhead having a plurality of differently sized and spaced ribs;
   a tray system configured to hold a stack of sheets below the feedhead;
   a vacuum source for providing a vacuum between the feedhead and the topmost sheet of the stack of sheets which differently corrugates the topmost sheet against said differently sized and spaced ribs of said sheet corrugator feedhead depending on the topmost sheet beam strength;
   at least one sensor configured to sense said corrugation of the topmost sheet and produce at least one sensor output corresponding to the topmost sheet corrugation; and
   a control program configured to select at least one preferred operating parameter of said vacuum corrugating sheet feeding system according to said at least one sensor output and predetermined rules.

7. The vacuum corrugating sheet feeder system according to claim 1 further comprising a system memory in which said predetermined rules are stored for selecting the at least one preferred operating parameter.

8. The vacuum corrugating sheet feeder system according to claim 1, further including at least one of an air knife output and a sheet fluffer output, wherein the control program is configured to select between at least one of two sets of preferred operating parameters and to adjust at least one of the vacuum source, the air knife output and the fluffer output.

9. The vacuum corrugating sheet feeder system according to claim 1 wherein the predetermined rules comprise a lookup table.

10. The vacuum corrugating sheet feeder system according to claim 9 further including a lookup program that receives the at least one sensor output, looks up the at least one preferred operating parameter in the lookup table, and performs appropriate adjustments to the vacuum corrugating sheet feeder system.

* * * * *